(12) United States Patent
Cadran et al.

(10) Patent No.: US 11,148,983 B2
(45) Date of Patent: Oct. 19, 2021

(54) TANTALUM-BASED CATALYST DEPOSITED ON SILICA FOR THE TRANSFORMATION OF ETHANOL INTO BUTADIENE

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Nicolas Cadran, Oullins (FR); Alexandra Chaumonnot, Lyons (FR)

(73) Assignees: IFP Energies nouvelles, Rueil-Malmaison (FR); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 378 days.

(21) Appl. No.: 15/745,292

(22) PCT Filed: Jul. 5, 2016

(86) PCT No.: PCT/EP2016/065823
§ 371 (c)(1),
(2) Date: Jan. 16, 2018

(87) PCT Pub. No.: WO2017/009107
PCT Pub. Date: Jan. 19, 2017

(65) Prior Publication Data
US 2018/0208522 A1 Jul. 26, 2018

(30) Foreign Application Priority Data
Jul. 13, 2015 (FR) ........................................ 1556662

(51) Int. Cl.
| | | |
|---|---|---|
| *C07C 1/20* | (2006.01) | |
| *B01J 37/06* | (2006.01) | |
| *B01J 21/08* | (2006.01) | |
| *B01J 23/20* | (2006.01) | |
| *B01J 37/02* | (2006.01) | |
| *B01J 29/03* | (2006.01) | |
| *B01J 35/10* | (2006.01) | |
| *B01J 37/08* | (2006.01) | |

(52) U.S. Cl.
CPC .............. *C07C 1/20* (2013.01); *B01J 21/08* (2013.01); *B01J 23/20* (2013.01); *B01J 29/0341* (2013.01); *B01J 35/1019* (2013.01); *B01J 35/1023* (2013.01); *B01J 35/1061* (2013.01); *B01J 37/0207* (2013.01); *B01J 37/06* (2013.01); *B01J 37/08* (2013.01); *C07C 2521/08* (2013.01); *C07C 2523/20* (2013.01)

(58) Field of Classification Search
CPC .... B01J 21/08; B01J 23/6486; B01J 35/1019; B01J 35/1023; B01J 37/0207; B01J 37/0205; B01J 37/0217; B01J 37/08; B01J 23/02; B01J 23/06; B01J 23/20; B01J 23/48; B01J 23/682; B01J 23/8476; C07C 1/20; C07C 2521/08; C07C 2523/18
USPC ........................................................ 502/246
See application file for complete search history.

(56) References Cited

U.S. PATENT DOCUMENTS

| | | | | |
|---|---|---|---|---|
| 4,240,931 A | * | 12/1980 | Milberger ................ | B01J 23/28 502/306 |
| 4,689,315 A | * | 8/1987 | Anton ...................... | B01J 21/08 423/335 |
| 5,780,680 A | * | 7/1998 | Eller ....................... | C07C 209/60 564/485 |
| 7,518,014 B2 | * | 4/2009 | Kimmich ................ | C07C 67/055 560/241 |
| 2003/0133868 A1 | * | 7/2003 | Bonneviot .............. | C01B 13/14 423/592.1 |
| 2008/0125610 A1 | * | 5/2008 | Lockemeyer ........... | C07C 41/02 564/503 |
| 2009/0178955 A1 | * | 7/2009 | Ryu ........................ | B01J 27/125 208/120.01 |
| 2011/0196185 A1 | * | 8/2011 | Krawczyk ............... | B01J 21/08 585/646 |
| 2013/0289133 A1 | * | 10/2013 | Doshita ................... | C01B 33/12 514/769 |
| 2014/0343306 A1 | * | 11/2014 | Rizkalla ................... | B01J 23/50 549/536 |
| 2016/0228851 A1 | * | 8/2016 | Hermans .................. | C07C 5/48 |

FOREIGN PATENT DOCUMENTS

| | | | |
|---|---|---|---|
| JP | 2010-013365 | * | 1/2010 |
| KR | 2014047329 A | | 4/2014 |
| KR | 2014050531 | * | 4/2014 |
| KR | 2014050531 A | | 4/2014 |

OTHER PUBLICATIONS

JP2010-013365 Translation (Year: 2010).*
International Search Report PCT/EP2016/065823 dated Nov. 2, 2016.

* cited by examiner

*Primary Examiner* — Patricia L. Hailey
(74) *Attorney, Agent, or Firm* — Millen White Zelano & Branigan

(57) ABSTRACT

The invention concerns a catalyst comprising at least the element tantalum, and at least one mesoporous oxide matrix that has undergone an acid wash comprising at least 90% by weight of silica before washing, the mass of the element tantalum being in the range 0.1% to 30% of the mass of said mesoporous oxide matrix.

19 Claims, No Drawings

TANTALUM-BASED CATALYST DEPOSITED ON SILICA FOR THE TRANSFORMATION OF ETHANOL INTO BUTADIENE

PRIOR ART

Butadiene is widely used in the chemical industry, in particular as a reagent for the production of polymers. Currently, butadiene is almost entirely produced from steam cracking units in which it constitutes an upgradable by-product. The fluctuation in the price of oil and the ever-increasing demand for this chemical intermediate have made its price very volatile, which has ignited a diversification of supply means. Thus, it is well known to the person skilled in the art that 1,3-butadiene can be produced from ethanol. Two processes have been industrialized on a large scale: the "S. K. Process" and the "Carbide Process". In the "S. K. Process", the 1,3-butadiene produced from ethanol in a single step, while in the "Carbide Process", the 1,3-butadiene is produced in two steps: ethanol is initially converted into acetaldehyde, then an ethanol-acetaldehyde mixture is converted into 1,3-butadiene. The principal distinction between the catalysts employed in these processes is that one (SK process) is capable of dehydrogenating the ethanol to acetaldehyde while producing butadiene from the mixture formed thereby, while the other is not, hence the need for a first step for dehydrogenation over a specific catalyst. The the most effective chemical elements that constitutes the catalyst for this method for the production of butadiene are magnesium, tantalum, zirconium and hafnium, with selectivities for butadiene of between 50% and 69%, niobium (or colombium) being considered to be a less attractive element with selectivities of below 40% (B. B. Corson, H. E. Jones, C. E. Welling, J. A. Hinckley, E. E. Stahly, *Ind. Eng. Chem.*, 1950, 42 (2), p 359-373).

Irrespective of the process (one or two steps), the overall balance for the principal reaction is written as follows:

$$2CH_3CH_2OH \rightleftharpoons CH_2CHCHCH_2 + H_2 + 2H_2O$$

Behind this overall balance there are many chemical reactions, including a reaction for dehydrogenation in order to generate acetaldehyde (I), a reaction for aldolisation/crotonisation of the acetaldehyde into crotonaldehyde (II), a Merwein-Pondorff-Verley (MPV) reaction between ethanol and crotonaldehyde (III), and finally a step for dehydration of the crotyl alcohol to form butadiene (IV).

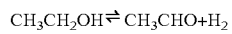
$$CH_3CH_2OH \rightleftharpoons CH_3CHO + H_2 \qquad \text{I:}$$

$$2CH_3CHO \rightleftharpoons CH_3CHCH{-}CHO + H_2O \qquad \text{II:}$$

$$CH_3CHCH{-}CHO + CH_3CH_2OH \rightleftharpoons CH_3CHCH{-}CH_2OH + CH_3CHO \qquad \text{III:}$$

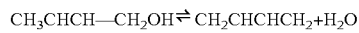
$$CH_3CHCH{-}CH_2OH \rightleftharpoons CH_2CHCHCH_2 + H_2O \qquad \text{IV:}$$

This multiplicity of chemical reactions is the source of many by-products if the sequence of steps is not carried out in the order set out above, in particular with the presence of dehydration reactions and secondary condensation reactions. In addition, other reactions may occur (such as isomerization, cyclization, Diels-Alder reaction, etc), further increasing the number of by-products. At this stage, it should be noted that, depending on the nature of the catalyst employed for the transformation of ethanol (or of ethanol-acetaldehyde mixture) into 1,3-butadiene, the distribution of said by-products may change significantly. Thus, adding an acidic element will increase the production of dehydration products (for example ethylene or diethylether), while adding a basic element will favour the formation of multiple condensation products (for example hexenes or hexadienes).

Consequently, irrespective of the process (one or two steps), the selectivity for the transformation of ethanol (or of ethanol-acetaldehyde mixture) into 1,3-butadiene is moderate. However, because of the relatively high price of the starting material, an economic study of the process shows that the efficiency for transformation of the feed constitutes an important tool to ensure its viability. A great deal of effort has thus been expended in maximizing this selectivity.

In particular, during the development of the process for the production of butadiene from an ethanol/acetaldehyde mixture (two-step process), the best discovered catalyst was a tantalum oxide deposited on an amorphous silica (Ind. Eng. Chem., 1949, 41, p 1012-1017). The selectivity for butadiene was 69% for an initial conversion of the feed of 34%. It was also shown that using the same catalyst in a "Carbide" industrial unit resulted in the formation of the following major impurities (by-products): diethyl ether (23% by weight of impurities), ethylene (11% by weight of impurities), hexenes, hexadienes (11% by weight of impurities), etc. (W. J. Toussaint, J. T. Dunn, D. R. Jackson, Industrial and Engineering Chemistry, 1947, 39 (2), p 120-125). Despite the presence of by-products, their formation is limited by the relatively low acid-base properties of the element tantalum. This latter can also catalyse reactions II, III and IV very effectively. One of its only disadvantages is its price.

Indeed, according to the report written in 2012 by Jonathan Burla, Ross Fehnel, Philip Louie and Peter Terpeluk of the University of Pennsylvania entitled "TWO-STEP PRODUCTION OF 1,3-BUTADIENE FROM ETHANOL", the price of silica is about $0.96/lb and that of tantalum is about $162/lb. By way of indication, the current prices for niobium and zirconium are about $20/lb and $1/lb, i.e. a price ratio of about one order of magnitude between niobium and tantalum and two orders of magnitude between zirconium and tantalum.

A variety of studies were then carried out in order to optimize the efficiency of tantalum and/or substitute this element. The patent U.S. Pat. No. 2,421,361 (W. J. Toussaint, J. T. Dunn, Carbide and Carbon Chemical Corporation, 1947) describes a process for the preparation of butadiene, that comprises the transformation of an acyclic mono-olefinic aldehyde (crotonaldehyde or acetaldehyde) and a monohydroxylated alcohol (ethanol) over a catalyst from the group formed by zirconium oxide, tantalum oxide, niobium oxide and one of the combinations of these oxides with silica. However, according to the provided examples, tantalum oxide used alone remains the best catalyst for converting the specific ethanol/acetaldehyde mixture. According to Ind. Eng. Chem., 1950, 42 (2), p 359-373, the best associations for the transformation of the ethanol/acetaldehyde mixture are: Ta—Cu, Ta—Zr, Zr—Nb, Zr—Ti and Zr—Th deposited on a silica support (patents U.S. Pat. Nos. 2,374,433, 2,436,125, 2,438,464, 2,357,855, 2,447,181). More recently, the majority of recent studies have sought to completely eliminate tantalum from the catalytic formulation, in particular by using the element zirconium or magnesium:

- the application WO 2014/199349 (BASF) uses a Zr, Zn, Cu association,
- the application WO 2014/180778 (Synthos) claims a Zr, Zn, La association,
- the application WO 2014/049158 (Lanxess) uses a mixed Mg—Si oxide doped with elements such as Ti, V, Mo, Mn, Cu, Ni, Zn or Cr, the application WO 2013/125389 (Daicel) claims the use of a mixed Mg—Si oxide doped with a metal from columns 4 to 13, the application WO 2012/015340 (Unisit) uses an association of an element in the metallic state from column 11 and a metal oxide selected from magnesium, titanium, zirconium, tantalum and niobium.

It should be noted that, irrespective of the research direction selected by the person skilled in the art to improve the performances of the catalyst under consideration, the support of choice for all of the materials being studied is a mesoporous silica support. Some studies have thus been focussed on improving the support. Thus, the application WO 2014/061917 seeks to improve the catalyst based on tantalum by using a silica support characterized by mesopores with uniform size and morphology and regularly distributed within the material (what is known as a mesostructured silica).

Acid washing of silicas is a method which is known to the person skilled in the art for modifying the performances of chromatographic columns by eliminating certain undesirable impurities (J. Nawrocki, Chromatographia, 1991, 31 (3/4), "Silica Surface Controversies, Strong Adsorption Sites, their Blockage and Removal. Part I"). In catalysis, this technique was used in the case of the metathesis of olefins (US 2011196185A (UOP LLC)) in the presence of a catalyst comprising tungsten dispersed on a support comprising silica, in order to improve the activity of the catalyst without degrading their selectivity. However, this particular implementation cannot easily be transposed. Thus, for example, while the productivity of a Nb-silica catalyst is improved when the support is washed with an acid, its selectivity in the reaction for the production of 1,3-butadiene is substantially degraded.

SUMMARY OF THE INVENTION

The invention concerns a catalyst comprising, and preferably constituted by, at least the element tantalum, and at least one mesoporous oxide matrix based on silica which has undergone an acid wash, said matrix comprising at least 90% by weight of silica before washing, the mass of tantalum being in the range 0.1% to 30% of the mass of said mesoporous oxide matrix.

The invention further concerns a process for the preparation of a catalyst, comprising at least the following steps:

a) at least one step for acid washing of a mesoporous oxide matrix that comprises at least 90% by weight of silica before washing, the percentages by weight being expressed with respect to the total mass of the mesoporous oxide matrix, with at least one organic acid and/or inorganic acid, at a temperature in the range 0° C. to 120° C. and with a contact time for said acid solution with said mesoporous oxide matrix in the range 10 min to 10 h, b) at least one step for heat treatment of said washed matrix obtained from step a) to obtain a catalyst support, c) at least one step for depositing at least one metallic precursor of at least the element tantalum onto the surface of said support obtained at the end of step b), and d) at least one step for heat treatment of the solid obtained from step c).

The invention also concerns a process for the preparation of a catalyst, comprising at least the following steps:

a') at least one step for depositing at least one metallic precursor of at least the element tantalum onto the surface of a mesoporous oxide matrix that comprises at least 90% by weight of silica before washing, the percentages by weight being expressed with respect to the total mass of the mesoporous oxide matrix, b') at least one step for heat treatment of the solid obtained from step a'), c') at least one step for acid washing of the solid obtained from step b'), with at least one organic acid and/or inorganic acid, at a temperature in the range 0° C. to 120° C., and with a contact time for said acid solution with said solid in the range 10 min to 10 h, d') at least one step for heat treatment of the solid obtained from step c').

The invention also concerns the use of the catalyst in accordance with the invention, for the conversion of a feed comprising at least ethanol into butadiene, at a temperature in the range 300° C. to 400° C., at a pressure in the range 0.15 to 0.5 MPa, and at a space velocity in the range 0.5 to 5 $h^{-1}$.

IMPORTANCE OF THE INVENTION

Compared with the prior art mentioned above, the present invention proposes an original approach for improving the potential of a catalyst for the production of butadiene starting from a mixture comprising at least ethanol, by means of a specific and appropriate pre-treatment of the support with a silica nature which is conventionally employed: an acid wash. This wash does not only involve the elimination of some potential impurities of the support, but also modifies its surface chemistry, which results in better activity of the tantalum based catalyst as well as an improvement in its selectivity. Another effect of the invention is an improvement in the productivity and selectivity for butadiene for the same feed flow rate.

DISCLOSURE OF THE INVENTION

The invention concerns a catalyst used for the production of butadiene, starting from a feed comprising at least ethanol, comprising at least the element tantalum, that is likely to implement at least the reactions II to IV mentioned above, and at least one mesoporous oxide matrix based on silica which has undergone an acid wash.

The catalyst in accordance with the invention comprises a mesoporous oxide matrix based on silica washed by bringing said matrix into contact with at least one acid, in particular an organic and/or an inorganic acid. Preferably, the acid that is used is an inorganic acid, optionally diluted in an aqueous solution. Particular inorganic acids include nitric acid, sulphuric acid and hydrochloric acid, with nitric acid and hydrochloric acid being preferred. The concentration of the used inorganic acid is generally in the range from 0.05 molar (M) to 3 M, and preferably in the range 0.1 M to 1 M. Said acid wash may be carried out under static conditions (for example as a "batch") or continuous conditions (for example circulation in a washing column with or without a partial or total recycle of the effluent). In accordance with the invention, the conditions representative of this acid washing are a temperature that is generally in the range 0° C. to 120° C., preferably in the range 15° C. to 80° C., and more preferably in the range 20° C. to 70° C. The time for contact of the acid solution with the mesoporous oxide matrix may vary between 10 minutes and 10 hours, and preferably between 30 minutes and 3 hours. An optional rinsing operation with water may then be carried out in order to eliminate the excess of acidity. This may be carried out under the same conditions as those described above.

The catalyst in accordance with the invention comprises a mass of Ta in the range 0.1% to 30%, preferably in the range 0.3% to 10%, more preferably in the range 0.5% to 5% and highly preferably in the range 0.5% to 2% of the mass of said mesoporous oxide matrix.

The term "catalyst comprising an element A, the mass of the element A being in the range x % to y %, or representing between x % and y %, of the mass of the mesoporous oxide matrix" means that said catalyst comprises said element A in the range x to y parts by weight per 100 parts by weight of said mesoporous oxide matrix.

The catalyst in accordance with the invention advantageously further comprises at least one element selected from the group consisting of elements from groups 2, 3, 4 and 5 of the periodic table and their mixtures, preferably selected from the group consisting of the elements from groups 2 and 5 of the periodic table and their mixtures, and more preferably at least one element selected from the group consisting of the elements Ca and Ba from group 2 and Nb from group 5 of the periodic table and their mixtures, the mass of said element being in the range 0.01% to 5%, preferably in the range 0.01% to 1%, more preferably in the range 0.05% to 0.5% of the mass of the mesoporous oxide matrix based on silica.

In a particular arrangement, the catalyst in accordance with the invention advantageously further comprises at least one element selected from the group consisting of groups 11 and 12 of the periodic table and their mixtures, i.e. the periodic classification of the elements, more preferably at least one element selected from group 12 of the periodic table, and yet more preferably the element Zn, the mass of said element being in the range 0.5% to 10% and preferably in the range 1% to 5% of the mass of said mesoporous oxide matrix based on silica. This arrangement is particularly advantageous in case of using the catalyst in accordance with the invention in a one-step process, i.e. in a process treating a feed comprising mainly ethanol. The expression "mainly ethanol" means that the weight ratio of ethanol to acetaldehyde in said feed, when said feed comprises acetaldehyde, is at least greater than 1, preferably at least greater than 5; said feed might not comprise acetaldehyde.

The mesoporous oxide matrix based on silica that has undergone a step for acid washing of the catalyst in accordance with the invention is called the "catalyst support" in the text of the present invention below.

The term "mesoporous oxide matrix based on silica" means a mesoporous oxide matrix comprising, before washing in accordance with the invention, at least 90% by weight with respect to the total mass of the mesoporous oxide matrix of silica. Preferably, before washing said matrix comprises silica in an amount of at least 95% by weight (i.e. from 95% up to 100%) with respect to the total mass of the mesoporous oxide matrix, more preferably at least 98% by weight (i.e. from 98% up to 100%) and yet more preferably at least 99.5% by weight (i.e. from 99.5% up to 100%).

In addition to silica, the mesoporous oxide matrix based on silica used in accordance with the invention advantageously contains, before washing, at least oxides of the following non-exhaustive list: zirconia, titanium oxide, boron oxide, lanthanum oxide and cerium oxide. Preferably, the mesoporous oxide matrix used in accordance with the invention contains, before washing, titanium oxide in addition to silica. Additionally, the mesoporous oxide matrix based on silica comprised in the catalyst in accordance with the invention optionally comprises at least one element of the following non-exhaustive list: Na, K, Mg, Ca, Al, Cu, Zn, Fe, Ni, Co, S, P. Advantageously, the mesoporous oxide matrix based on silica comprised in the catalyst in accordance with the invention comprises at least one element of the group consisting of Na, K, Mg, Ca, Al, Cu, Zn, Fe, Ni, Co, S and P, and mixtures thereof. Before washing, the mesoporous oxide matrix based on silica advantageously comprises more than 500 ppm of alkali metals.

Before washing, the mesoporous oxide matrix based on silica comprised in the catalyst in accordance with the invention is mesoporous, i.e. it is characterized by the presence of pores with a size in the range 2 to 50 nm in accordance with the IUPAC classification (K. S. W. Sing, D. H. Everett, R. A. Haul, L. Moscou, J. Pierotti, J. Rouquerol, T. Siemieniewska, *Pure Appl. Chem.*, 1985, 57, 603). In addition to being mesoporous, said matrix may be mesostructured (i.e. having mesopores with uniform size and regularly distributed within said matrix), or it may have a hierarchical porosity (presence of micropores and/or macropores in addition to mesopores). The use of well-known mesostructured silicas, such as the silicas SBA15 and MCM41, enables to take advantage of the very high specific surface areas developed by this type of solid (between 600 and 1200 m$^2$/g).

Highly preferably, the mesoporous oxide matrix based on silica comprised in the catalyst in accordance with the invention is, before washing, a mesoporous amorphous silica with an unorganized porosity without micropores. As an example, it is possible to use Davisil Grade 636 or 646 silicas sold by WR Grace & Co., Columbia, Md., which are also known as "silica gels" because they are obtained by precipitation at a pH 7, commercial silicas known as precipitated silicas, obtained using a pH 7, or commercial silicas known as fumed silicas, obtained by hydrolysis of $SiCl_4$ at 1000° C. It is also possible to customize the synthesis of the silica using methods known to the person skilled in the art, in particular by using "traditional" inorganic synthesis methods (precipitation/gelling from salts under mild temperature and pressure conditions) or "modern" organo-metallic methods (precipitation/gelling from alkoxides under mild temperature and pressure conditions). Particularly advantageous results have thus been obtained after acid washing a mesoporous oxide matrix based on silica that, before washing, is characterized by a specific surface area of at least 250 m$^2$/g, preferably by a specific surface area in the range 250 m$^2$/g to 700 m$^2$/g and more preferably by a specific surface area in the range 400 m$^2$/g to 600 m$^2$/g. In addition, before washing, the mean pore diameter (or pore size) of the mesoporous oxide matrix based on silica used in accordance with the invention is preferably at least 4 nm, more preferably in the range 4.5 to 50 nm and yet more preferably in the range 4.5 to 20 nm.

In general, the process for the preparation of the catalyst in accordance with the invention comprising at least the element tantalum and at least one mesoporous oxide matrix based on silica that has undergone an acid wash comprises a) acid washing of the mesoporous oxide matrix based on silica, b) heat treatment of said washed matrix obtained from step a) to obtain the catalyst support in accordance with the invention, c) depositing at least one metallic precursor of at least the element tantalum on the surface of said support obtained at the end of step b), and d) heat treatment of the solid obtained from step c) to obtain the catalyst in accordance with the invention.

In accordance with step a) or a') of the process for the preparation of the catalyst in accordance with the invention, the mesoporous oxide matrix based on silica is as described in the present text pertaining to the invention. In particular, said matrix may be commercial or custom-synthesized using methods known to the person skilled in the art. In addition, said mesoporous oxide matrix based on silica may be used directly in the form of powder or already shaped, in particular in the form of pelletized, crushed and screened powder, beads, pellets, granules or extrudates (hollow or non-hollow cylinders, multi-lobed cylinders with 2, 3, 4 or 5 lobes for example, twisted cylinders) or rings, etc, these shaping operations being carried out using techniques well-known the person skilled in the art. Preferably, said mesoporous oxide matrix based on silica is obtained in the form of extrudates with size in the range 1 to 10 mm. However, it is not excluded for said obtained mesoporous oxide matrix based on silica to be then, for example, introduced into equipment to round the surface, such as a bowl granulator or any other equipment to spheronize them.

In accordance with step a) of the process for the preparation of the catalyst in accordance with the invention, the used mesoporous oxide matrix based on silica is washed by bringing said matrix into contact with at least one acid, in particular an organic acid and/or an inorganic acid. Preferably, the used acid is an inorganic acid, optionally diluted in an aqueous solution. Particular inorganic acids include nitric acid, sulphuric acid and hydrochloric acid, with nitric acid and hydrochloric acid being preferred. The concentration of the used inorganic acid is generally in the range 0.05 molar (M) to 3 M and preferably in the range 0.1 M to 1 M. Said acid wash may be carried out under static conditions (for example as "batch"), or continuous conditions (for example circulation in a washing column with or without a partial or complete recycle of the effluent). In accordance with the invention, representative conditions for this acid wash are a temperature generally in the range 0° C. to 120° C., preferably in the range 15° C. to 80° C., and highly preferably in the range 20° C. to 70° C. The contact time for the acid solution with the mesoporous oxide matrix may vary between 10 minutes and 10 hours and preferably between 30 minutes and 3 hours. An optional operation for rinsing with water may then be performed in order to eliminate the excess of acidity. This may be carried out under the same conditions as described above. This operation is needed when the acid cannot be easily eliminated during steps b) and d) of the process for the preparation of the catalyst in accordance with the invention, this latter having then risks to be present on the final catalyst. These conditions apply mutatis mutandis to the solid obtained from step b') in step c') of the preparation process in accordance with the invention.

This step for acid washing is crucial to improve the potential of a catalyst for the production of butadiene starting from a mixture comprising at least ethanol, in that it induces the elimination of some potential impurities from the support and/or modifies the surface chemistry, which results in better activity of the catalyst as well as an improvement in its selectivity.

At the end of this operation and before impregnation of the active element(s), the catalyst contains small amounts of sodium in the range 0 to 500 ppm, preferably in the range 0 to 300 ppm and more preferably in the range 0 to 100 ppm.

In accordance with step b) of the process for the preparation of the catalyst in accordance with the invention, the mesoporous oxide matrix based on washed silica obtained from step a) of the process for the preparation of the catalyst in accordance with the invention undergoes at least one heat treatment to open up the pores of said matrix. This treatment corresponds to drying, calcining and/or steaming of said washed matrix, using methods that are well known to the person skilled in the art. Preferably, said treatment is carried out in a range of temperature of 50° C. to 800° C., preferably 80° C. to 800° C. and highly preferably 80° C. to 300° C., for a period of less than 72 h and preferably less than 24 h. These conditions apply mutatis mutandis to step d').

In accordance with step c) of the process for the preparation of the catalyst in accordance with the invention, at least one step for depositing at least one metallic precursor of at least the element tantalum onto the surface of said support obtained at the end of step b) is carried out using any of the synthesis methods known to the person skilled in the art. As an example and in a non-exhaustive manner, the methods known as dry impregnation, excess impregnation, CVD (Chemical Vapour Deposition), CLD (Chemical Liquid Deposition), etc, may be employed. As an example, in the case of a deposition carried out by the dry impregnation method, step c) of the process for the preparation of the catalyst in accordance with the invention is constituted by the following individual operations: dissolving at least one precursor of at least the element tantalum in a volume of solution corresponding to the pore volume of the support obtained at the end of step b) of the preparation process in accordance with the invention, impregnation of said solution onto the surface of said support and optional maturation of the solid obtained thereby in a controlled atmosphere and at a controlled temperature to favour the dispersion of at least said precursor used in accordance with the invention over the whole of the surface of the support.

In accordance with step c) of the process for the preparation of the catalyst in accordance with the invention, the metallic precursor of at least the element tantalum is any compound comprising at least the element tantalum and that can release this element in solution in a reactive form. Thus, the precursors of at least the element tantalum are advantageously inorganic salts and alkoxide precursors. The inorganic salts are selected from the group consisting of halides, nitrates, sulphates, phosphates, hydroxides, carbonates, carboxylates, alcoholates and combinations of two or more thereof, more preferably selected from the group consisting of chlorides, nitrates, carboxylates, alcoholates and combinations of two or more thereof. The alkoxide precursors have, for example, the formula $M(OR)_n$ where M=Ta and R=ethyl, isopropyl, n-butyl, s-butyl, t-butyl, etc. or a chelated precursor such as $X(C_5H_8O_2)_n$, with n=3 or 4. As an example, the preferred precursors of tantalum are tantalum pentachloride and tantalum pentaethanoate that may be used with the majority of organic solvents. The conditions of step c) apply mutatis mutandis to step a').

In accordance with step d) of the process for the preparation of the catalyst in accordance with the invention, the solid obtained from step c) of the process for the preparation of the catalyst in accordance with the invention then undergoes at least one step for heat treatment in order to obtain the catalyst in accordance with the invention. This treatment corresponds to drying, calcining and/or steaming said washed matrix, using methods well known to the person skilled in the art. Preferably, the treatment is drying followed by calcining. The drying phase is carried out by circulating a gas at a temperature in the range 50° C. to 200° C. and preferably in the range 80° C. to 150° C. over the solid, for a period lasting from 1 to 24 hours. Preferably, said drying step is carried out in air flow. The calcining phase is carried out by circulating a gas at a temperature in the range 350° C. to 700° C., preferably in the range 450° C. to 600° C. over the dried solid, for a period lasting from 1 to 6 h and preferably in the range 2 to 4 h. Said calcining step is carried out in a stream of gas comprising oxygen. The conditions for step d) apply mutatis mutandis to step b').

When the mesoporous oxide matrix based on silica needed for step a) or a') of the process for the preparation of the catalyst in accordance with the invention is used as a powder form that is not shaped, the catalyst in accordance with the invention, that is itself not shaped at the end of step d) or d') of the preparation process of the invention, may be shaped into the form of a pelletized, crushed, screened powder, beads, pellets, granules or extrudates (hollow or non-hollow cylinders, multi-lobed cylinders with 2, 3, 4 or 5 lobes, for example, or twisted cylinders) or rings, etc, these shaping operations being carried out using techniques well known to the person skilled in the art. Preferably, said catalyst used in accordance with the invention is obtained in form of extrudates with a size in the range 1 to 10 mm. However, this does not exclude said obtained materials being subsequently, for example, introduced into equipment to round their surfaces, such as a bowl granulator or any other equipment to spheronize them.

During said shaping operation, the catalyst in accordance with the invention may optionally be mixed with at least one porous oxide material acting as a binder to generate the physical properties of the catalyst, that are suitable for the process (mechanical strength, wear resistance, etc).

Said porous oxide material is preferably a porous oxide material selected from the group formed by silica, magnesia, clays, titanium oxide, lanthanum oxide, cerium oxide, phosphates of boron and a mixture of at least two of the oxides cited above. It is also possible to use titanates, for example zinc, nickel or cobalt titanates. It is also possible to employ simple, synthetic or natural clays of the dioctahedral 2:1 phyllosilicate or trioctahedral 3:1 phyllosilicate type such as kaolinite, antigorite, chrysotile, montmorillonnite, beidellite, vermiculite, talc, hectorite, saponite, or laponite. These clays may optionally have been delaminated. The various mixtures using at least two of the compounds cited above are further suitable for acting as a binder.

Highly preferably, the used binder has the nature of a silica. By way of non-exhaustive example, said silica binder may be in the form of powders or colloidal solutions.

Preferably, said catalyst comprises 5% to 60% by weight, and more preferably in the range 10% to 30% by weight of silica binder, the percentages by weight being expressed with respect to the total mass of said catalyst.

Optionally, at least one organic adjuvant is also mixed in during said shaping step. The presence of said organic adjuvant facilitates shaping by extrusion. Said organic adjuvant may advantageously be selected from methyl cellulose, hydroxypropylmethyl cellulose, hydroxyethyl cellulose, carboxymethyl cellulose and polyvinyl alcohol. The proportion of said organic adjuvant is advantageously in the range 0 to 20% by weight, preferably in the range 0 to 10% by weight and more preferably in the range 0 to 7% by weight with respect to the total mass of said shaped material.

In the particular case of shaping the catalyst in accordance with the invention following step d) for heat treatment in the preparation process, said post-treatment step is carried out again after shaping.

To finish, the optional addition of at least one element from groups 2, 3, 4, 5, 11 and 12 of the periodic table may be carried out using any of the methods known to the person skilled in the art and at any of the steps for the synthesis and/or shaping of the used mesoporous oxide matrix based on silica or of the catalyst in accordance with the invention.

The two processes in accordance with the invention differ only in the order the washing step is carried out, namely either in step a) prior to depositing the metallic precursor of at least the element tantalum, or in step c') that follows the deposition of said metallic precursor. These two processes are alternatives that can overcome the same technical problem of preparing a catalyst with improved performances.

The textural parameters mentioned above are determined using the analytical technique known as "nitrogen volumetry", corresponding to the physical adsorption of molecules of nitrogen into the pores of a material by slowly increasing the pressure at constant temperature. The term "specific surface area" means the BET specific surface area ($S_{BET}$ in $m^2/g$), determined by the adsorption of nitrogen in accordance with the standard ASTM D 3663-78 based on the BRUNAUER-EMMETT-TELLER method described in the journal *"The Journal of the American Society"*, 1938, 60, 309. The pore distribution that is representative of a population of mesopores is determined using the Barrett-Joyner-Halenda (BJH) model. The obtained nitrogen adsorption-desorption isotherm in accordance with the BJH model is described in the journal *"The Journal of the American Society"*, 1951, 73, 373, by E. P. Barrett, L. G. Joyner and P. P. Halenda. The pore volume V is defined as the value corresponding to the volume observed for the partial pressure $P/P^0_{max}$ of the nitrogen adsorption-desorption isotherm. In the disclosure of the invention below, the term "nitrogen adsorption volume" means the volume measured for $P/P^0_{max}=0.99$, at which pressure it is assumed that the nitrogen has filled all of the pores. In the disclosure below, the mesopores diameter ϕ of the mixed oxide in accordance with the invention is determined using the formula $4000 \cdot V/S_{BET}$.

In the disclosure of the invention below, the pore distribution measured by mercury porosimetry is determined by mercury porosimetry intrusion in accordance with the standard ASTM D4284-83 at a maximum pressure of 4000 bar (400 MPa), using a surface tension of 484 dyne/cm and a contact angle of 140°. The wetting angle was taken to be equal to 140°, following the recommendations in the publication "Techniques de l'ingénieur, traité analyse and caractérisation [Engineering Techniques: analysis and characterization], P 1050-5, by Jean Charpin and Bernard Rasneur".

The value beyond which the mercury fills all of the intergranular voids was fixed at 0.2 MPa; beyond this, the mercury is assumed to penetrate into all of the pores of the solid.

In order to obtain better precision, the value for the total pore volume corresponds to the value for the total pore volume measured by mercury intrusion porosimetry for the sample minus the value for the total pore volume measured by mercury intrusion porosimetry measured for the same sample at a pressure corresponding to 30 psi (approximately 0.2 MPa).

The macroporous volume of the catalyst is defined as the cumulative volume of mercury introduced at a pressure in the range 0.2 MPa to 30 MPa, corresponding to the volume contained in pores with an apparent diameter greater than 50 nm.

The mesoporous volume of the catalyst is defined as the cumulative volume of mercury introduced at a pressure in the range 30 MPa to 400 MPa, corresponding to the volume contained in pores with an apparent diameter in the range 2 to 50 nm.

The volume of the micropores is measured by nitrogen porosimetry. The quantitative analysis of the microporosity is carried out using the "t" method (Lippens-De Boer method, 1965), corresponding to a transform of the initial adsorption isotherm, as described in the publication "Adsorption by powders and porous solids. Principles, methodology and applications" by F. Rouquerol, J. Rouquerol and K. Sing, Academic Press, 1999.

The median diameter of the mesopores (Dp, in nm) is also defined as a diameter such that all of the pores with a size smaller than this diameter constitute 50% of the mesoporous volume, measured by mercury porosimetry.

Using a washed mesoporous oxide matrix based on silica as a support for a catalyst comprising at least the element tantalum for the conversion of a feed comprising at least ethanol into butadiene results in significant performance advantages in terms of catalytic activity, of conversion degree obtained at a given reaction temperature and/or of selectivity. The representative conditions for this reaction are a temperature in the range 300° C. to 400° C., preferably in the range 320° C. to 380° C., a pressure in the range 0.15 to 0.5 MPa, preferably in the range 0.15 to 0.3 MPa, and a space velocity in the range 0.5 to 5 $h^{-1}$, preferably in the range 1 to 4 $h^{-1}$. When the treated feed further comprises acetaldehyde, the ethanol/acetaldehyde weight ratio is in the range 1 to 30, preferably in the range 2 to 10. The space velocity is defined as the ratio between the mass flow rate of the feed and the mass of the catalyst.

The invention will now be illustrated by means of the following examples.

EXAMPLES

Definition of Terms $$WHSV(g/g_{Ta}/h): WHSV = \frac{\text{mass flow rate of feed} \left(\frac{g}{h}\right)}{\text{mass of tantalum } (gTa)}$$

Productivity ($g_c/g_{Ta}/h$):

$$\text{productivity} = \frac{\text{mass flow rate of carbon belonging to butadiene} \left(\frac{gc}{h}\right)}{\text{mass of tantalum present on catalyst } (gTa)}$$

Selectivity (% C):

$$\text{selectivity} = \frac{\text{mass flow rate of carbon belonging to butadiene} \left(\frac{gc}{h}\right)}{\text{mass flow rate of carbon belonging to converted feed}}$$

Example 1—Preparation of the Silica 12.5 mL of a solution of 68% (by volume) nitric acid are added to a solution containing 55 mL of tetraethylorthosilicate (TEOS, $Si(OCH_2CH_3)_4$) and 150 mL of ethanol, at ambient temperature. The mixture is stirred for 30 min. 50 mL of a 14% (by volume) ammoniacal solution is then added. The system become cloudy and a gel is formed. 19 mL of ethanol are then added to enable additional stirring for 3 hours. The final gel is filtered, washed with ethanol then dried at 100° C. for 24 hours. The obtained silica powder is then calcined in air at 550° C. for 4 hours.

The characteristics of the used mesoporous oxide matrices in the examples are summarized below.

TABLE 1

| Mesoporous oxide matrix | BET specific surface area ($m^2/g$) | Mean pore diameter (nm) | WU (mL/g) | Presence of alkali metals |
|---|---|---|---|---|
| Merck 7734 | 550 | 6 | 0.8 | >500 ppm |
| Davisil 636 | 507 | 7 | 1 | >500 ppm |
| Davisil 646 | 300 | 15 | 1.2 | >500 ppm |
| Silica synthesized in accordance with Example 1 | 690 | 15 | 1.5 | <100 ppm |

Example 2—Washing of Mesoporous Oxide Matrix

The various mesoporous oxide matrices described in Table 1 (granulometry: 250-500 μm) are placed on a No. 4 frit over which a washing solution is passed for 1 hour. The used volume of the solution represents around 5 times the volume occupied by the mesoporous oxide matrix. The washed solids are rinsed with an equivalent volume of distilled water for 1 additional hour, then are placed in an oven at 115° C. for at least 4 hours.

The characteristics of the mesoporous oxide matrices after washing are summarized in Table 2.

TABLE 2

| Silica support | BET specific surface area ($m^2/g$) | Mean pore diameter (nm) | Pore volume (mL/g) | Presence of alkali metals |
|---|---|---|---|---|
| Merck 7734 | 570 | 6 | 0.8 | <500 ppm |
| Davisil 636 | 512 | 7 | 1 | <500 ppm |
| Davisil 646 | 320 | 14 | 1.2 | <500 ppm |
| Silica synthesized in Example 1 | 620 | 13 | 1.5 | <100 ppm |

The acid wash described above induces decreasing the alkali contents to less than 1000 ppm for all of the silica supports and slightly modifies the texture of the supports.

Example 3—Dry Impregnation of Supports in Order to Deposit Tantalum

Tantalum pentaethoxide ($Ta(OCH_2CH_3)_5$) (the amount of which is calculated from the amount of Ta to be deposited onto the support) is diluted in a solution of ethanol (the amount of which is proportional to the pore volume of the silica support). This solution is rapidly added drop by drop and mixed with the silica support until the wetness is observed on the surface thereof (dry impregnation). The solid is then placed in an atmosphere saturated with ethanol for 3 hours, then dried at 100° C. for 24 hours. The catalyst is obtained by calcining the dried solid in air at 550° C. for 4 hours.

Example 4—Dry Impregnation in Order to Deposit Niobium

Ammonium niobium oxalate pentahydrate (the amount of which is calculated from the amount of Nb to be deposited on the support) is diluted to form an aqueous solution (the amount of which is proportional to the pore volume of the silica support). This solution is rapidly added drop by drop and mixed with the silica until the wetness is observed on the surface thereof (dry impregnation). The solid is then placed in an atmosphere saturated with ethanol for 3 hours, then dried at 100° C. for 24 hours. The catalyst is obtained by calcining the dried solid in air at 550° C. for 4 hours.

Example 5—Dry Impregnation in Order to Deposit Zirconium

Zirconyl chloride (the amount of which is calculated from the amount of Zr to be deposited on the support) is diluted to form an aqueous solution (the amount of which is proportional to the pore volume of the silica, support). This solution is rapidly added drop by drop and mixed with the silica until the wetness is observed on the surface thereof (dry impregnation). The solid is then placed in an atmosphere saturated with ethanol for 3 hours, then dried at 100° C. for 24 hours. The catalyst is obtained by calcining the dried solid in air at 550° C. for 4 hours.

Table 3 provides an overview of the prepared catalysts.

TABLE 3

| Catalyst | In accordance with the invention? Y/N | Starting silica | Washing solution | Metal and impregnated quantity |
|---|---|---|---|---|
| A | N | Davisil 636 | — | 0.5% Ta |
| B | Y | Davisil 636 | HCl 1N | 0.5% Ta |
| C | N | Davisil 636 | — | 2% Ta |
| D | Y | Davisil 636 | HCl 0.1N | 2% Ta |
| E | Y | Davisil 636 | HCl 1N | 2% Ta |
| F | N | Davisil 646 | — | 2% Ta |
| G | Y | Davisil 646 | HCl 0.1N | 2% Ta |
| H | N | Merck 7734 | — | 0.5% Ta |
| I | N | Merck 7734 | water | 0.5% Ta |
| J | Y | Merck 7734 | HCl 0.1N | 0.5% Ta |
| K | N | Synthesized silica | — | 2% Ta |
| L | Y | Synthesized silica | HCl 0.1N | 2% Ta |
| M | N | Davisil 636 | — | 2% Nb |
| N | N | Davisil 636 | HCl 1N | 2% Nb |
| O | N | Davisil 636 | — | 2% Zr |
| P | N | Davisil 636 | HCl 1N | 2% Zr |
| Q | Y | 2% Ta/Davisil 636 | HCl 0.1N | — |

Description of the Catalytic Test Unit

The reactor used in the examples below consists of a 20 cm long stainless steel tube with a diameter of 10 mm. The reactor is initially charged with carborundum, then with catalyst diluted in carborundum, and finally with carborundum. Carborundum is inert regarding the feed and has no influence on the catalytic results; it is used to position the catalyst in the isothermal zone of the reactor and to limit the risk of problems relating to heat and matter transfer. The temperature of the reactor is controlled with a tube furnace with three heating zones. The liquid feed (mixture of ethanol and acetaldehyde in a proportion R) is injected using a twin piston HPLC pump. The liquid stream is vaporized in the heated lines by a tracer before entering the reactor and is homogenized by passage through a static mixer. The products formed during the reaction are kept in the vapour phase so that they can be analysed in-line using gas chromatography (PONA and Carboxen 1010 capillary columns) in order to identify the hundreds of products formed as accurately as possible. The catalyst is activated in situ in nitrogen at the test temperature. The specific operating conditions are described in the following examples.

Example 6—Impact of Acid Washing on Catalysts Comprising Tantalum

In this test, the ethanol/acetaldehyde ratio of the charge is fixed at 2.6 (mol/mol), the temperature at 350° C. and the pressure at 0.15 MPa. For each catalyst, the flow rate of the feed is adjusted to obtain a constant WHSV of 250 $g/g_{Ta}/h$.

The values for selectivity and carbon productivity are measured at this point of the operation.

The impact of the acid wash on catalysts based on tantalum is demonstrated by the results summarized in Table 4.

TABLE 4

| Catalyst | In accordance with the invention? Y/N | Butadiene productivity (gC/gTa/h) | Gain in productivity (%) | Selectivity | Gain in selectivity |
|---|---|---|---|---|---|
| A | N | 27 | — | 66% | — |
| B | Y | 39 | +44% | 72% | +6 |
| C | N | 37 | — | 72% | — |
| D | Y | 42 | +14% | 74% | +2 |
| E | Y | 43 | +16% | 74% | +2 |
| F | N | 18 | — | 65% | — |
| G | Y | 33 | +83% | 69% | +4 |
| H | N | 11 | — | 57% | — |
| I | N | 11 | 0% | 60% | +3 |
| J | Y | 40 | +263% | 72% | +15 |
| K | N | 35 | — | 73% | — |
| L | Y | 42 | +20% | 74% | +1 |

Acid washing of the mesoporous oxide matrix before impregnation of the element tantalum leads to increase the butadiene productivity and selectivity of the catalyst for all of the used mesoporous oxide matrices compared to the catalysts with identical tantalum contents but for which the mesoporous oxide matrix has not undergone any acid wash, or for which the mesoporous oxide matrix has only undergone a wash with water.

Example 7—Impact of Acid Wash on Catalysts Based on Niobium or Zirconium, not Containing the Element Tantalum

TABLE 5

| Catalyst | In accordance with the invention? Y/N | Butadiene productivity (gC/gM/h) | Gain in productivity (%) | Selectivity | Gain in selectivity |
|---|---|---|---|---|---|
| M | N | 33 | — | 57% | — |
| N | N | 40 | +21% | 45% | −12 |
| O | N | 60 | — | 63% | — |
| P | N | 72 | +20% | 63% | 0 |

Catalysts M and N are obtained by impregnating 2% Nb onto a Davisil 636 silica. It can be seen that acid washing the silica improves the productivity, but that the selectivity of these catalysts not containing the element tantalum is substantially degraded.

Catalysts O and P are obtained by impregnating 2% Zr onto a Davisil 636 silica. An improvement in productivity is observed, but there is no effect of acid wash of the silica on the selectivity for these catalysts which do not contain the element tantalum.

Thus, associating acid washing and the presence of the element tantalum results in a gain in selectivity and also in productivity for the production of 1,3-butadiene.

Example 8—Impact of the Order of the Preparation Steps for Catalysts Based on Tantalum

| Catalyst | In accordance with the invention? Y/N | Butadiene productivity (gC/gM/h) | Gain in productivity (%) | Selectivity | Gain in selectivity |
|---|---|---|---|---|---|
| C | N | 37 | — | 72% | — |
| D | Y | 42 | +14% | 74% | +2 |
| Q | Y | 39 | +7% | 74% | +2 |

Acid washing the solid after depositing the active phase based on tantalum further results in better performances. This result is surprising, because a change in the active phase would have been expected.

The invention claimed is:

1. A catalyst comprising at least the element tantalum, and at least one mesoporous oxide matrix based on silica that has undergone an acid wash, wherein said matrix comprises at least 90% by weight of silica before washing, wherein the mass of tantalum is in the range 0.1% to 30% of the mass of said mesoporous oxide matrix, wherein said wash is carried out by contacting with an inorganic acid that is nitric acid, sulfuric acid or hydrochloric acid, at a concentration in the range 0.05 M to 3 M, at a temperature in the range 0° C. to 120° C. and with a contact time in the range 10 min to 10 h.

2. The catalyst as claimed in claim 1, wherein said at least one mesoporous oxide matrix is an amorphous mesoporous silica with an unorganized porosity without micropores.

3. The catalyst as claimed in claim 1, wherein before washing, said at least one mesoporous oxide matrix has a specific surface area in the range 250 $m^2/g$ to 700 $m^2/g$.

4. The catalyst as claimed in claim 1, wherein said oxide matrix is mesostructured.

5. The catalyst as claimed in claim 1, further comprising at least one element selected from the group consisting of the elements from groups 2, 3, 4 or 5 of the periodic table and mixtures thereof, the mass of said element being in the range 0.01% to 5% of the mass of said at least one mesoporous oxide matrix.

6. The catalyst as claimed in claim 5, comprising at least one element selected from the group consisting of the elements from groups 2 and 5 of the periodic table and mixtures thereof, the mass of said element being in the range 0.01% to 5% of the mass of said at least one mesoporous oxide matrix.

7. The catalyst as claimed in claim 6, comprising at least one element selected from the group consisting of the elements Ca, Ba and Nb and mixtures thereof, the mass of said element being in the range 0.01% to 5% of the mass of said at least one mesoporous oxide matrix.

8. The catalyst as claimed in claim 1, further comprising at least one element selected from the group consisting of groups 11 and 12 of the periodic table and mixtures thereof, the mass of said element being in the range 0.5% to 10% of the mass of said at least one mesoporous oxide matrix.

9. The catalyst as claimed in claim 8, further comprising at least the element Zn, the mass of said element being in the range 0.5% to 10% of the mass of said at least one mesoporous oxide matrix.

10. A process for the preparation of a catalyst as claimed in claim 1, comprising at least:

a) at least one acid washing of a at least one mesoporous oxide matrix comprising at least 90% by weight of silica before washing, the percentage by weight being expressed with respect to the total mass of the at least one mesoporous oxide matrix, with at least one inorganic acid that is nitric acid, sulfuric acid or hydrochloric acid, at a concentration in the range 0.05 M to 3 M, at a temperature in the range 0° C. to 120° C. and with a contact time for said acid solution with said at least one mesoporous oxide matrix in the range 10 min to 10 h, b) at least one heat treatment at 80° C. to 300° C., for less than 72 h, of said washed matrix obtained from a) to obtain a catalyst support, c) at least one deposit of at least one metallic precursor of at least the element tantalum onto the surface of said support obtained at the end of b), and d) at least one heat treatment of solid obtained from c), said heat treatment being drying followed by calcining, wherein the drying is carried out by circulating a gas at a temperature of 80° C. to 150° C. over solid obtained from c), for 1 to 24 hours, and the calcining is carried out by circulating a gas containing oxygen, at a temperature of 450° C. to 600° C., over dried solid, for 1 to 6 h.

11. A process for the preparation of a catalyst as claimed in claim 1, comprising at least:

a') at least one step for depositing at least one metallic precursor of at least the element tantalum onto the surface of a at least one mesoporous oxide matrix comprising at least 90% by weight of silica before washing, the percentage by weight being expressed with respect to the total mass of the at least one mesoporous oxide matrix, b') at least one heat treatment of solid obtained from a') said heat treatment being drying followed by calcining, wherein the drying is carried out by circulating a gas at a temperature of 80° C. to 150° C. over solid obtained from a'), for 1 to 24 hours, and the calcining is carried out by circulating a gas containing oxygen, at a temperature of 450° C. to 600° C., over dried solid, for 1 to 6 h, c') at least one acid washing of the solid obtained from b') with at least one inorganic acid that is nitric acid, sulfuric acid or hydrochloric acid, at a concentration in the range 0.05 M to 3 M, at a temperature in the range 0° C. to 120° C., and with a contact time for said acid solution with said solid in the range 10 min to 10 h, d') at least one heat treatment of the solid obtained from c'), wherein said heat treatment is carried out at a temperature of 80° C. to 300° C. for less than 72 h.

12. A process for the conversion of a feed comprising at least ethanol into butadiene comprising contacting said feed with a catalyst according to claim 1, at a temperature in the range 300° C. to 400° C., at a pressure in the range 0.15 to 0.5 MPa, and at a space velocity in the range 0.5 to 5 $h^{-1}$.

13. The process as claimed in claim 12, wherein the temperature is in the range 320° C. to 380° C.

14. The process as claimed in claim 12, wherein the pressure is in the range 0.15 to 0.3 MPa.

15. The process as claimed in claim 12, wherein the space velocity is in the range 1 to 4 $h^{-1}$.

16. A catalyst comprising at least the element tantalum, and at least one mesoporous oxide matrix based on silica that has undergone an acid wash, wherein said at least one mesoporous oxide matrix comprises at least 90% by weight of silica before washing, further comprises at least one oxide selected from the group consisting of zirconium oxide, titanium oxide, boron oxide, lanthanum oxide, cerium oxide and mixtures thereof, wherein the mass of tantalum is in the range 0.1% to 30% of the mass of said at least one mesoporous oxide matrix, wherein said wash is carried out by contacting with an inorganic acid that is nitric acid, sulfuric acid or hydrochloric acid, at a concentration in the range 0.05 M to 3 M, at a temperature in the range 0° C. to 120° C. and with a contact time in the range 10 min to 10 h.

17. A process for the preparation of a catalyst as claimed in claim 16, comprising at least:
 a) at least one acid washing of at least one mesoporous oxide matrix comprising at least 90% by weight of silica before washing, further comprising at least one oxide selected from the group consisting of zirconium oxide, titanium oxide, boron oxide, lanthanum oxide, cerium oxide and mixtures thereof, the percentages by weight being expressed with respect to the total mass of said at least one mesoporous oxide matrix, with at least one inorganic acid that is nitric acid, sulfuric acid or hydrochloric acid, at a concentration in the range 0.05 M to 3 M, at a temperature in the range 0° C. to 120° C. and with a contact time for said acid solution with said at least one mesoporous oxide matrix in the range 10 min to 10 h,
 b) at least one heat treatment of said washed matrix obtained from a) to obtain a catalyst support,
 c) at least one deposition of at least one metallic precursor of at least the element tantalum onto the surface of said support obtained at the end of b), and
 d) at least one heat treatment of solid obtained from c).

18. A process for the preparation of a catalyst as claimed claim 16, comprising at least:
 a') at least one deposition of at least one metallic precursor of at least the element tantalum onto the surface of at least one mesoporous oxide matrix comprising at least 90% by weight of silica before washing, further comprising at least one oxide selected from the group consisting of zirconium oxide, titanium oxide, boron oxide, lanthanum oxide, cerium oxide and mixtures thereof, the percentages by weight being expressed with respect to the total mass of the at least one mesoporous oxide matrix,
 b') at least one heat treatment of the solid obtained from a'),
 c') at least one acid washing of the solid obtained from b') with at least one inorganic acid that is nitric acid, sulfuric acid or hydrochloric acid, at a concentration in the range 0.05 M to 3 M, at a temperature in the range 0° C. to 120° C., and with a contact time for said acid solution with said solid in the range 10 min to 10 h,
 d') at least one heat treatment of solid obtained from c').

19. A catalyst consisting of the element tantalum, and at least one mesoporous oxide matrix based on silica that has undergone an acid wash, wherein said matrix comprises at least 90% by weight of silica before washing, wherein the mass of tantalum is in the range 0.1% to 30% of the mass of said at least one mesoporous oxide matrix, wherein said wash is carried out by contacting with an inorganic acid that is nitric acid, sulfuric acid or hydrochloric acid, at a concentration in the range 0.05 M to 3 M, at a temperature in the range 0° C. to 120° C. and with a contact time in the range 10 min to 10 h.

* * * * *